(12) United States Patent
Ingram et al.

(10) Patent No.: US 7,850,647 B2
(45) Date of Patent: Dec. 14, 2010

(54) SINGLE USE RETRACTABLE SYRINGE

(75) Inventors: Bruce Wallace Ingram, East Hawthorn (AU); Rupert Northcott, North Sydney (AU); Andrew Berry, Parkdale (AU)

(73) Assignee: Glenord Pty. Ltd. (AU)

( * ) Notice: Subject to any disclaimer, the term of this patent is extended or adjusted under 35 U.S.C. 154(b) by 370 days.

(21) Appl. No.: 10/592,713

(22) PCT Filed: Mar. 16, 2005

(86) PCT No.: PCT/AU2005/000371

§ 371 (c)(1),
(2), (4) Date: Jul. 1, 2008

(87) PCT Pub. No.: WO2005/089831

PCT Pub. Date: Sep. 29, 2005

(65) Prior Publication Data

US 2008/0262423 A1 Oct. 23, 2008

(51) Int. Cl.
*A61M 5/00* (2006.01)
(52) U.S. Cl. .................................................. 604/110
(58) Field of Classification Search ................. 604/110, 604/93.01
See application file for complete search history.

(56) References Cited

U.S. PATENT DOCUMENTS

| 5,106,379 A | | 4/1992 | Leap | |
|---|---|---|---|---|
| 5,338,303 A | * | 8/1994 | King et al. | 604/110 |
| 5,376,080 A | * | 12/1994 | Petrussa | 604/198 |
| 5,429,613 A | | 7/1995 | D'Amico | |
| 5,562,626 A | * | 10/1996 | Sanpietro | 604/110 |
| 6,569,115 B1 | * | 5/2003 | Barker et al. | 604/110 |
| 6,905,478 B2 | * | 6/2005 | Ingram et al. | 604/110 |
| 6,945,960 B2 | * | 9/2005 | Barker et al. | 604/198 |
| 7,497,847 B2 | * | 3/2009 | Crawford et al. | 604/198 |
| 2004/0116853 A1 | * | 6/2004 | Halseth et al. | 604/110 |
| 2004/0147875 A1 | * | 7/2004 | Wallace et al. | 604/110 |

(Continued)

FOREIGN PATENT DOCUMENTS

| EP | 1 334 740 | 8/2003 |
|---|---|---|
| WO | 02/072182 A1 | 9/2002 |

(Continued)

*Primary Examiner*—Nicholas D Lucchesi
*Assistant Examiner*—Victoria P Campbell
(74) *Attorney, Agent, or Firm*—Andrus, Sceales, Starke & Sawall, LLP

(57) ABSTRACT

A single use retractable syringe (10) has an inner barrel (44) supporting a needle (16) at one end and is slidable within an outer barrel (11). In the packaged condition the inner barrel is in a position relative to the outer barrel such that the needle can be attached to a Luer connection on the inner barrel and projects from a first end (18) of the outer barrel. The inner barrel has first and second latching means (40, 41, 43) adjacent each end, respectively, and the outer barrel has retaining means (48) on the inner wall surface adjacent the second end thereof. When the inner barrel first latching means (40) is engaged with the retaining means the syringe is in position ready for use and after the first full depression of a plunger the inner barrel is released and moves to a position where the second latching means (41, 43) becomes permanently engaged with the retaining means. The needle is then fully enclosed within the outer barrel and the inner barrel projects from the second end (19) of the outer barrel.

14 Claims, 14 Drawing Sheets

U.S. PATENT DOCUMENTS

2004/0230158 A1  11/2004  Malenchek
2005/0192533 A1*  9/2005  Lo .............................. 604/110
2006/0200077 A1*  9/2006  Righi et al. ................. 604/110

FOREIGN PATENT DOCUMENTS

WO    WO-03/101513    8/2003

* cited by examiner

SINGLE USE RETRACTABLE SYRINGE

CROSS REFERENCE TO RELATED APPLICATION

The present application is the U.S. national stage application of International Application PCT/AU2005/000371, filed Mar. 16, 2005, which international application was published on Sep. 29, 2005 as International Publication WO 2005/089831. The International Application claims priority of Australian Patent Application 2004901391, filed Mar. 16, 2004.

BACKGROUND OF THE INVENTION

The present invention relates to a single use retractable syringe generally as described in applicant's earlier International Application PCT/AU02/00297 and entitled "Improved non-reusable syringe" the contents of which are included herein by cross-reference. Specifically, the present invention relates to an improvement in the earlier device whereby the length of the syringe in the initial or non-retracted condition is significantly reduced.

Syringes of the retractable and/or single use type are well documented and serve to significantly reduce the risk of needle pricks to medical staff, in the case of retractable syringes, and eliminate re-use by intravenous drug users in the case of the single use type. Whilst the syringe of applicant's aforementioned earlier application satisfies both these objectives, it suffers a disadvantage in that the inner barrel remains within the outer barrel in both the initial and retracted positions and as a consequence the outer barrel, and hence the overall syringe, is longer than may be considered convenient by medical staff.

SUMMARY OF THE INVENTION

Accordingly, it is an object of this invention to provide a single use retractable syringe that is compact in size in the initial or packaged condition ready for use.

The invention provides a syringe comprising an outer barrel having first and second ends, an inner barrel slidable longitudinally within said outer barrel and adapted to support a needle at one end thereof, which needle projects through an aperture in said first end of said outer barrel and is in fluid communication with a fluid retaining chamber of said inner barrel, a piston within said chamber and actuable to draw fluid into said chamber and expel fluid from said chamber via said needle, a plunger connected to said piston and extending out from the other end of said inner barrel and the second end of said outer barrel, said outer barrel having retaining means on the inner wall surface thereof and said inner barrel having first and second spaced latching means for respectively engaging said retaining means and latching said inner barrel in either of two positions relative to said outer barrel, a first position wherein said needle projects from said outer barrel and is in a useable position, and a second position wherein said needle is fully retracted within said outer barrel, biasing means for biasing said inner barrel towards said second position and said plunger having means thereon to disengage said first latching means from said retaining means when said plunger is fully depressed whereby said inner barrel is able to move to said second position wherein said second latching means engages said retaining means and prevents further relative movement between said inner and outer barrels, and wherein a limit catch is provided on said plunger, said limit catch preventing said plunger from being fully depressed and disengaging said first latching means from said retaining means on initial actuation of said plunger but allowing said plunger to be depressed sufficiently to disengage said first latching means on the next plunger depression.

BRIEF DESCRIPTION OF THE DRAWINGS

In order that the invention may be more readily understood one particular embodiment will now be described with reference to the accompanying drawings wherein.

DETAILED DESCRIPTION OF THE INVENTION

Figure 1:
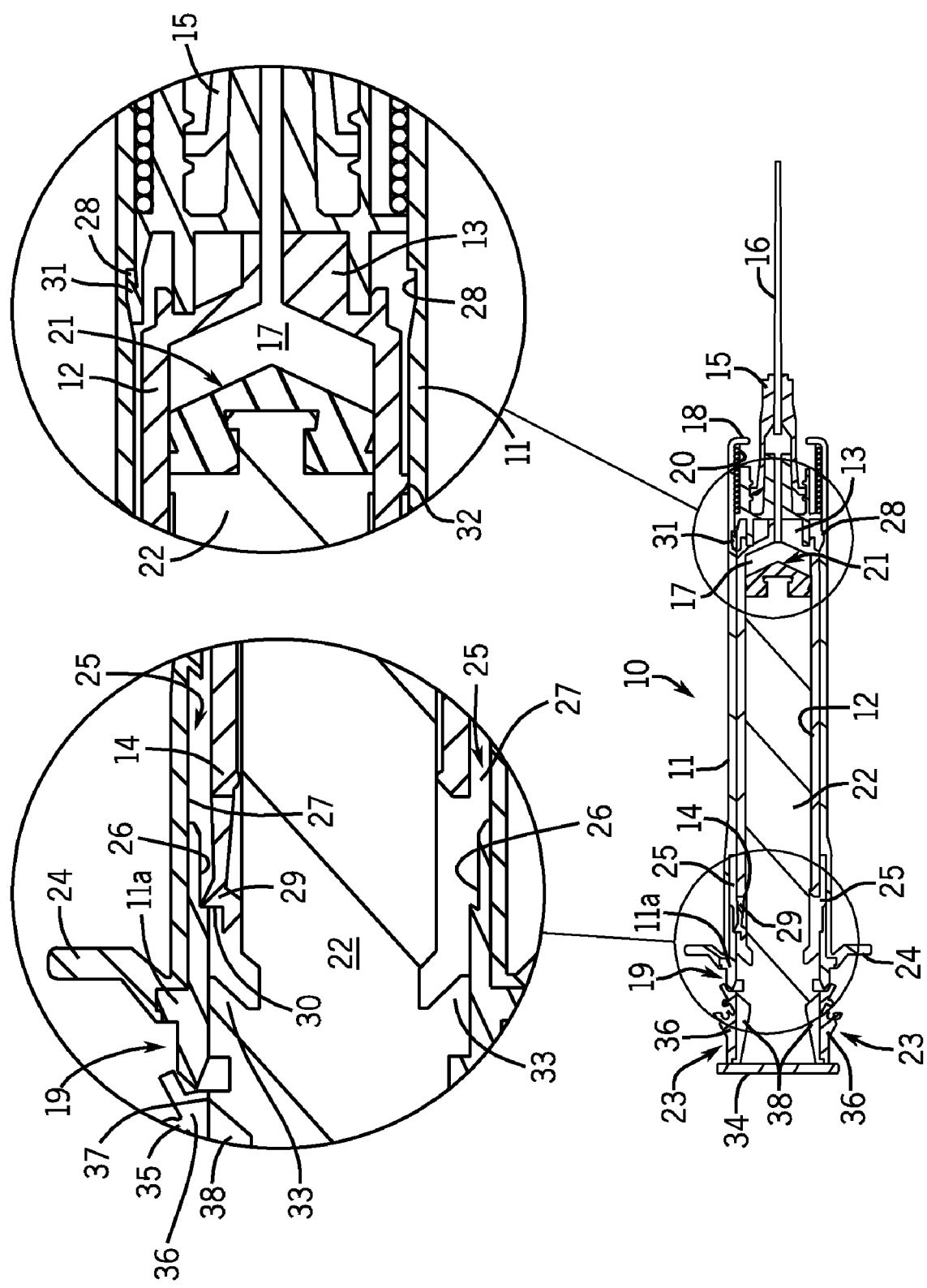
FIG. 1. is a sectional side elevation of a syringe according to the invention, in condition ready for use and showing respective ends of the syringe in larger scale.
Figure 2:
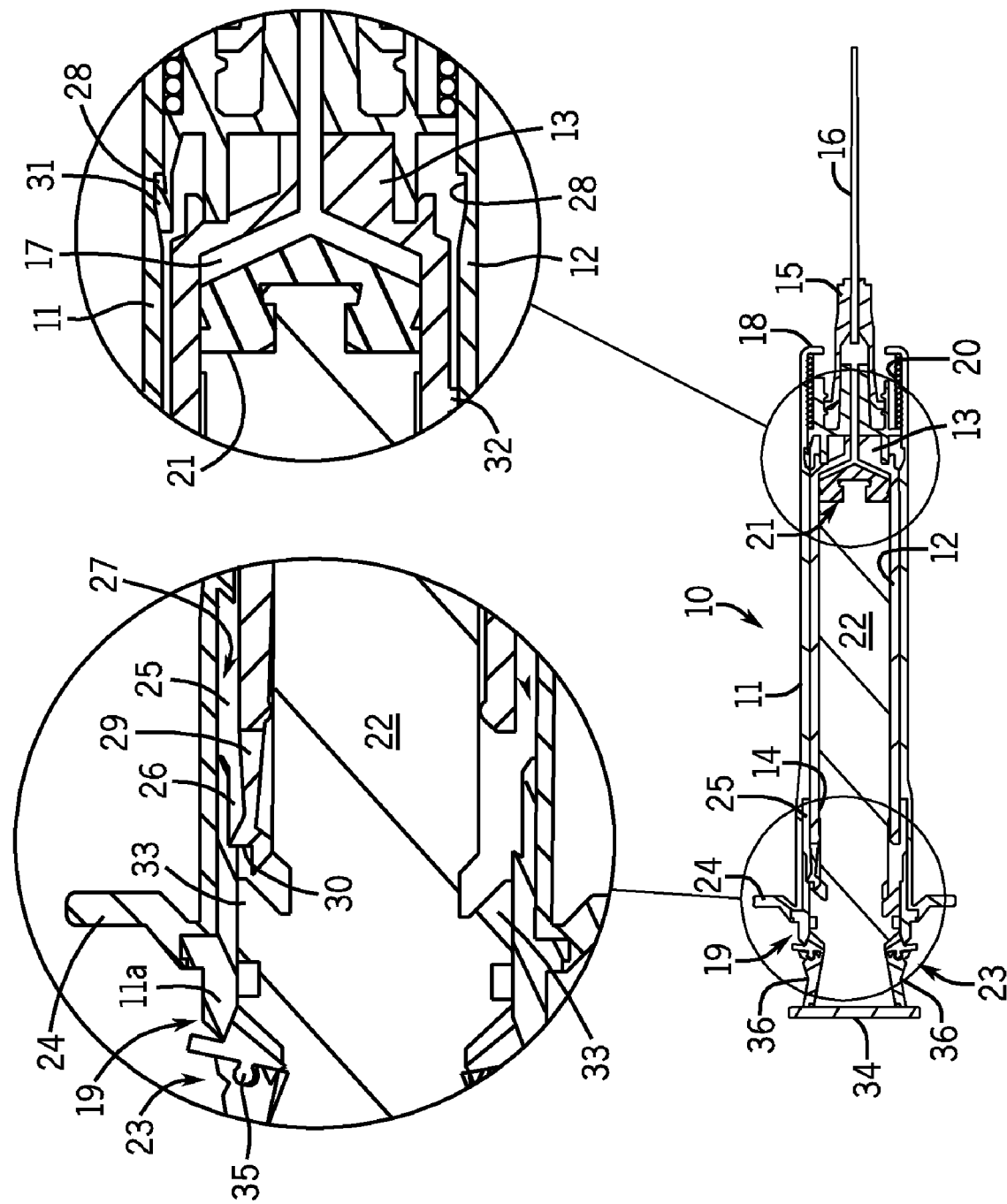
FIG. 2. is similar to FIG. 1 and shows the syringe in condition after initial depression of the plunger to break the piston seal.
Figure 3:
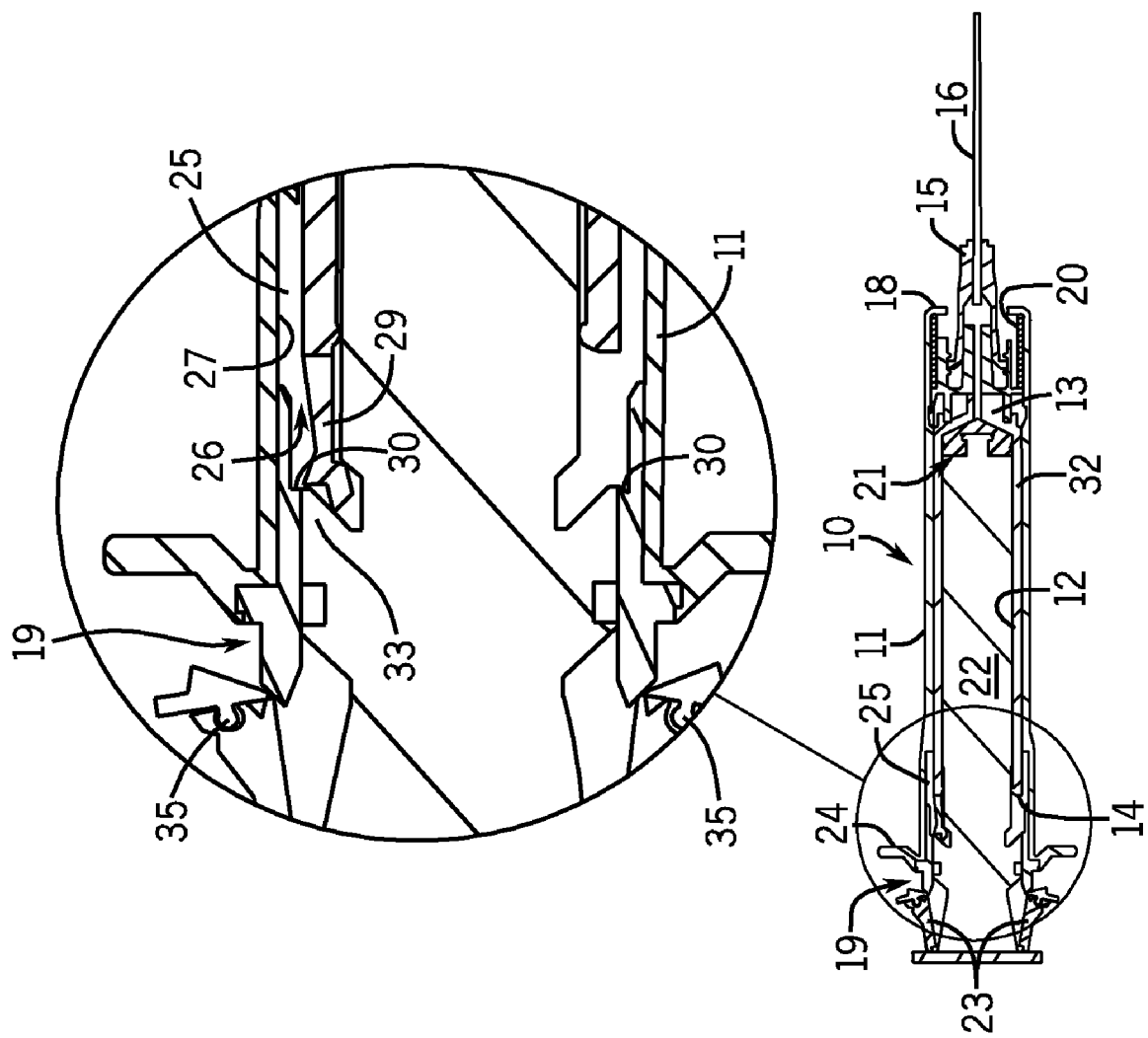
FIG. 3. is similar to FIG. 1 and shows the syringe, after completion of the injection stroke, at commencement of inner barrel and needle retraction.
Figure 4:
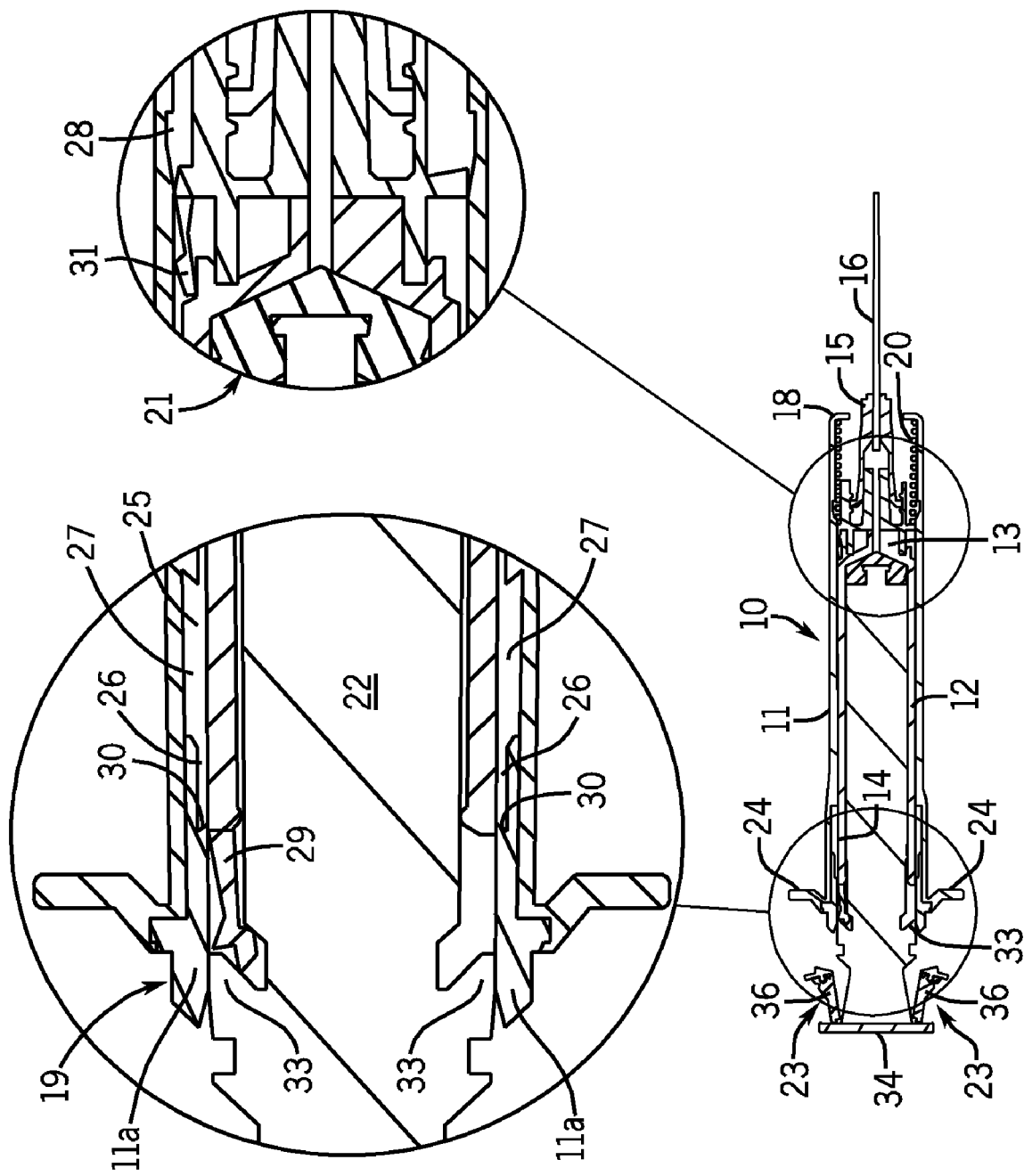
FIG. 4. is similar to FIG. 3 and shows the syringe after slight retraction of the inner barrel and needle.

Referring to FIGS. 1-7, the syringe 10 comprises an outer barrel 11 which, apart from openings at each end, is a completely aperture free cylindrical barrel. An inner barrel 12 fits within the outer barrel 11 in a manner so as to slide longitudinally back and forth within the outer barrel 11 in engagement therewith. The inner barrel 12 has a neck 13 at one end and is open at the opposite end 14. The neck 13 is adapted to engage with a needle housing 15 and the needle housing 15 incorporates a needle 16. The needle 16 is in fluid communication with a chamber 17 within the inner barrel 12 as is evident in the drawings. Once fitted to the neck 13, the needle 16 projects from a first end 18 of the outer barrel 11.

A spring 20 is located inside the first end 18 of the outer barrel and acts on the inner barrel 12 to bias the inner barrel 12 towards a second end 19 of the outer barrel 11.

A piston 21 is located within the inner barrel 12 and is mounted at one end of a plunger 22. The plunger 22 enters the second end 19 of the outer barrel and the open end 14 of the inner barrel. The outer end of the plunger 22 is provided with a limit catch 23 which will be described hereinbelow. A flange 24 at the second end 19 of the outer barrel facilitates operation of the syringe. An end flange 34 on the plunger 22 facilitates pressure by the users thumb in order to depress the plunger whilst holding the outer barrel between the first and second fingers located against the flange 24.

For convenience in manufacture, the outer barrel 11 is formed in two parts comprising the main cylindrical barrel referenced 11 and an insert 11A located in the second end 19 of the outer barrel. The purpose of the insert 11A is to facilitate provision of an annular groove 25 formed on the inside of the outer barrel in proximity of the second end 19. The annular groove 25 has a shallow portion 26 and a deeper portion 27 and the sides of the groove are inclined inwardly for purposes that will become apparent hereinbelow. A second annular groove 28 is provided in the inner wall of the outer barrel 11 towards the first end 18 thereof and the purpose of this second groove 28 will also become apparent hereinbelow.

The inner barrel 12 is also formed in two parts for convenience of manufacture and includes the main inner barrel 12 and the needle housing 15. The inner barrel 12 has three fingers 29 equally spaced around the circumference at the end 14 thereof. The fingers are cantilevered from the end 14 of the inner barrel and are resilient in that they may be flexed inwardly towards each other from their normal position. The fingers have a ledge 30 which engages an edge of the groove 25 to prevent the inner barrel from moving in a direction out of the end 19 of the outer barrel when the syringe is in the initial condition ready for use. This position is evident in FIG. 1 of the drawings.

The inner barrel 12 also has three fingers 31 at the opposite end to the fingers 29 and the fingers 31 are also equally spaced around the circumference of the barrel 12. The fingers 31 are also resilient and are accommodated in the annular groove 28 in the inner surface of the outer barrel 11 when the syringe is in the normal condition ready for use. The accommodation of the fingers 31 in the groove 28 is for no purpose other than to ensure that the fingers 31 are in the non-flexed condition during storage of the syringe prior to use, so that the fingers retain their resilience when forced inwardly towards each other.

The plunger 22 has an annular ridge or shelf 33 located towards the outer end thereof. The ridge or shelf 33 is adapted to contact the fingers 29 of the inner barrel 11 when the plunger is fully depressed at the end of an injection stroke. This contact causes the fingers 29 to flex inwardly and disengage from the groove 25. Once the fingers 29 disengage the groove 25 action of the spring 20 causes the inner barrel to move in a direction towards the second end 19 of the outer barrel whereby the inner barrel and hence the plunger are moved in a direction out of or away from the outer barrel 11. This causes the needle 16 to be retracted into the outer barrel as is shown in FIG. 5, for example.

Figure 5:
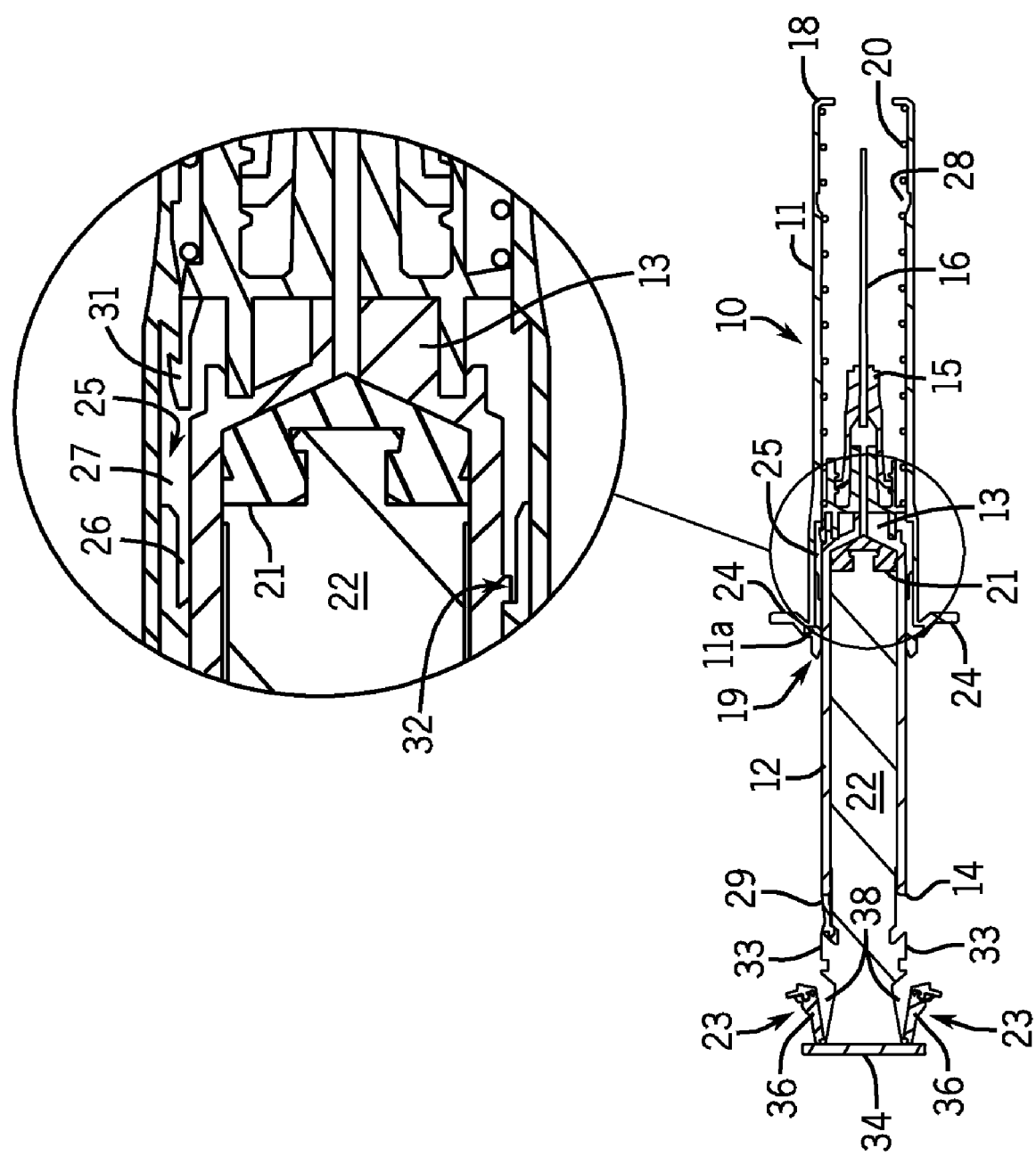
FIG. 5. is similar to the previous figures and shows the syringe in the fully retracted condition.

When the needle is fully retracted to the position shown in FIG. 5, the fingers 31 at the needle end of the inner barrel engage in the annular groove 25 in a manner preventing the inner barrel from moving back into the outer barrel. To prevent the inner barrel from being completely withdrawn from the outer barrel, abutments 32 on the outer surface of the inner barrel also engage in the annular groove 25 and thus a combination of the abutments 32 and the fingers 31 lock the inner barrel permanently in relation to the outer barrel in the position shown, for example in FIG. 5.

It only remains to describe a limit catch 23 located at the outer end of the plunger 22. The limit catch is fully described in applicant's aforementioned International Application PCT/AU02/00297 but will be described again here for convenience. The limit catch 23 prevents the plunger 22, and hence the piston 21, from moving to the forward or needle end extremity of the inner barrel 12 on the first operation of the syringe. Once the plunger 22 is forced inwardly towards the needle end of the syringe on the initial occasion (to break the plunger seal) the limit catch 23 changes its construction whereby, on the next depression of the plunger 22, the plunger is able to move to the forwardmost extremity of its movement in the inner barrel.

The limit catch 23 consists essentially of two diametrically opposed fingers 36 that initially engage the end 19 of the outer barrel 11. Each of the fingers 36 is attached to the end flange 34 of the plunger by a resilient hinge connection that biases the fingers outwardly away from the plunger 22. However, initially the other end of each finger is attached to the plunger by a membrane 37 not clearly evident in the drawings. Each finger 36 is formed essentially in two parts with a flexible joint between the parts and each finger spans a narrowing section of the plunger whereby a space or void 38 is formed on the inside of each finger for reasons that will become apparent. A tongue and groove 35 on the respective parts of the fingers 36 will lock the two parts in a different configuration once the membrane 37 is fractured and relative pivoting action occurs between the two parts.

As is evident in FIG. 1, in the initial or packaged condition of the syringe, the fingers 36 span the void 38 and make contact between the end flange 34 and the end 19 of the outer barrel 11 preventing full depression of the plunger. The first operation in using the syringe is to depress the plunger to break any seal that occurs between the piston 21 and the inner barrel due to the syringe having been stored for some time. This initial depression of the plunger causes the fingers 36 to pivot at the interconnection between the two parts whereby the tongue and groove between the two parts engages and the fingers move into the void 38 on their respective sides of the plunger. As is evident in FIG. 2, this movement causes the fingers to engage the end 19 of the outer barrel which prevents full depression of the plunger. Once the plunger is withdrawn and the fingers are free from the end 19 of the outer barrel, they pivot outwardly due to the bias of the flexible connection with the flange 34. This outward movement of the fingers means that on the next depression of the plunger, the fingers do not engage the end of the outer barrel in a manner that limits depression of the plunger (see FIG. 3). The plunger is therefore able to be fully depressed as occurs on the injection stroke whereby the ridge 33 engages the fingers on the inner barrel on full depression of the plunger and the inner barrel and hence the needle retract into the outer barrel.

Figure 7:
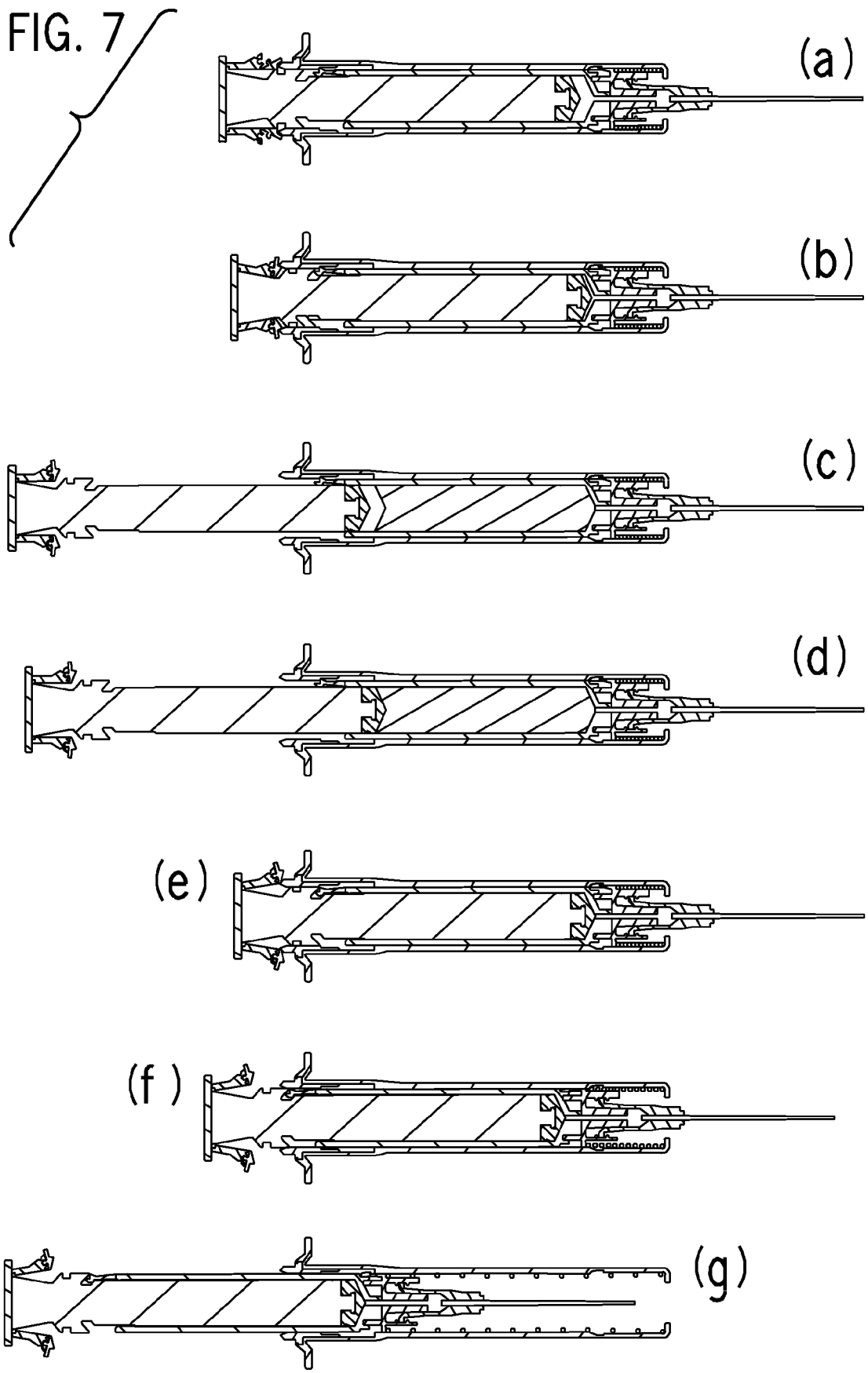
FIGS. 7a-7g are perspective views, on a reduced scale, showing the various stages of operation of the syringe.

Operation of the syringe will be readily apparent with reference to FIGS. 7 (*a*) to 7(*g*). The syringe is packaged after manufacture in a sealed package without the needle 16 and is in a condition where the inner barrel and plunger are in the position shown in FIG. 7 (*a*). The user removes the syringe from the package and attaches the needle onto a Luer lock of needle housing 15 of the inner barrel 12. The plunger 22 is then depressed to the position shown in FIG. 7 (*b*) where the limit catch 23 prevents full depression of the plunger. In this position the piston 21 is almost to the neck 13 of the inner barrel and only a very small chamber exists in the inner barrel between the piston 21 and the neck 13.

The next action is aspiration whereby a drug is drawn into the inner barrel 12 via the needle 16. The needle is placed in the fluid and the plunger is withdrawn outwardly to a position as shown in FIG. 7 (*c*). The inner barrel still remains firmly fixed relative to the outer barrel.

The next action is to depress the plunger slightly to remove any air from the chamber 17. The syringe is then in the position shown in FIG. 7(*d*). The syringe is then prepared and ready for the injection stage which is performed by full depression of the plunger 22 after the needle is inserted into the patient. Once the injection stage is completed the syringe is in the condition shown in FIG. 7 (*e*). On completion of the injection stage the user releases thumb pressure on the flange 34 and the plunger and inner barrel are forced outwardly from the outer barrel due to the force provided by spring 20. FIG. 7 (*f*) shows the initial part of this movement and FIG. 7 (*g*) shows the end result where the plunger and the inner barrel extend almost entirely out of the outer barrel 11. In this position the needle is fully retracted into the outer barrel and is safe from contact by medical personnel and others who may be susceptible to needle pricks. In this condition shown in FIG. 7 (*g*) the inner barrel is permanently locked in its position relative to the outer barrel and therefore further use of the syringe is prevented.

Figure 8:
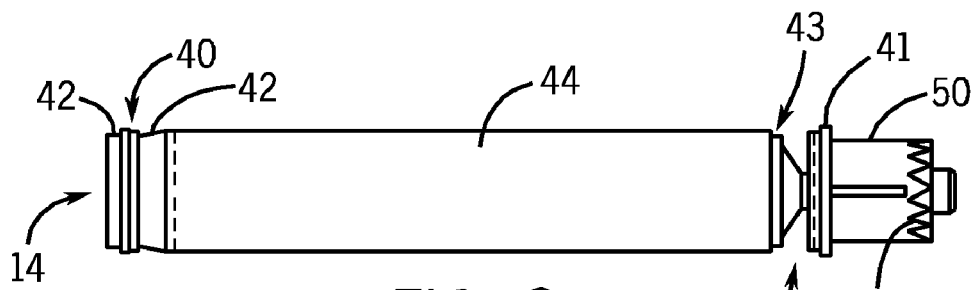
FIG. 8. is a side elevation of an inner barrel according to an alternative, more preferred embodiment of the invention.
Figure 9:
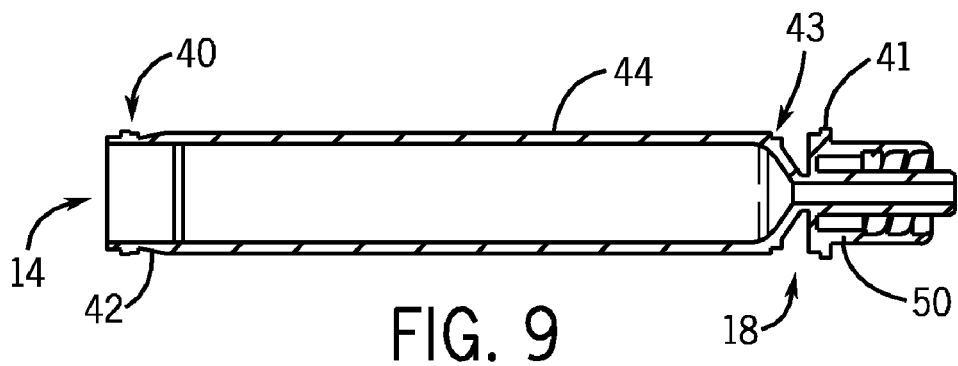
FIG. 9. is a sectional view of the inner barrel shown in FIG. 8.
Figure 10:
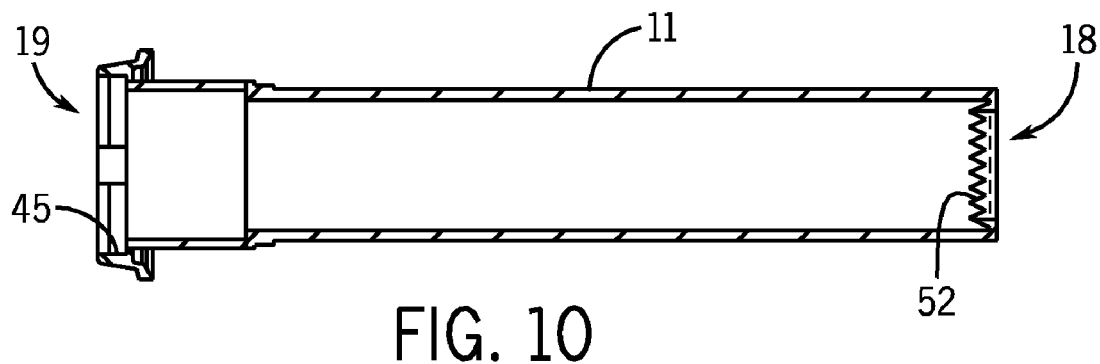
FIG. 10. is a sectional side elevation of an outer barrel according to the embodiment of FIGS. 8 and 9.
Figure 11:
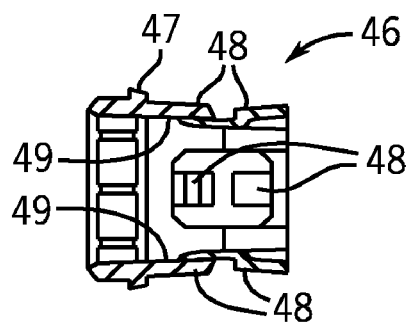
FIG. 11. is a sectional side elevation, of an insert for the outer barrel of FIG. 10.
Figure 12:
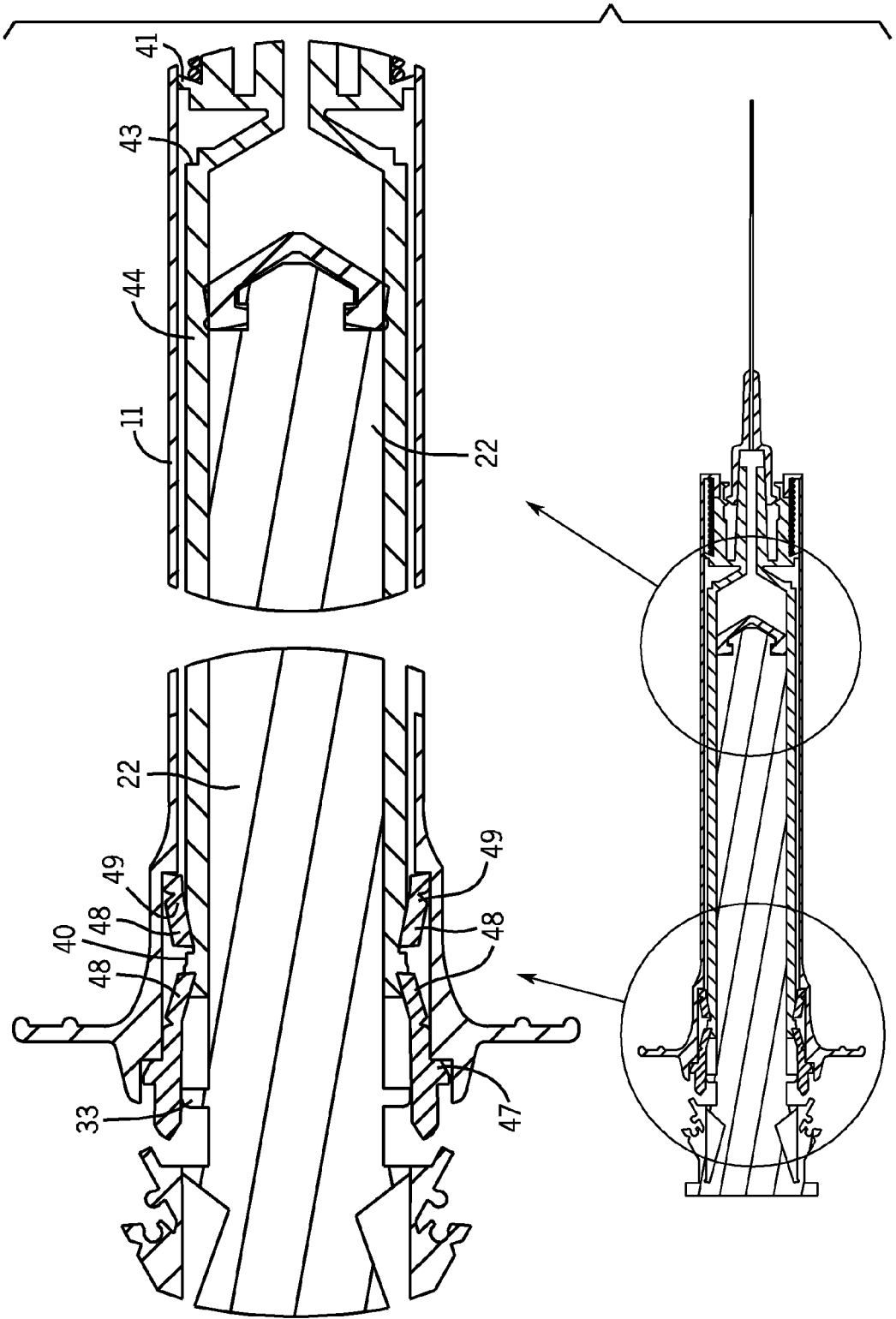
FIG. 12. is a sectional side elevation, on an enlarged scale, of the syringe according to the alternative embodiment, showing the relevant position of the parts when the syringe is ready for use with needle attached.

The alternative embodiment shown in FIGS. 8-17 differs from the first embodiment essentially for the purpose of ease of manufacture. As can be seen in FIGS. 8 and 9 the inner barrel 44 differs in that instead of the flexible fingers 29 and 31, the inner barrel has a stepped annular protrusion 40 that is arranged within a tapered groove 42, in the outer surface of the inner barrel adjacent the open end 14. This protrusion 40 replaces the fingers 29 and an annular step 43 at the other or inner end of the inner barrel 44 partly replaces the fingers 31.

The outer barrel 11 (FIG. 10) does not have a groove 28 adjacent the first end 18 and is very similar to the first embodiment at its second end 19. In other words at the second end 19 the outer barrel has a slightly enlarged internal bore and an annular groove 45 which is very much the same as in the first embodiment.

A further modification of the inner and outer barrels of this alternative embodiment is for the purpose of preventing relative rotation between the two barrels when they are in the initial or packaged condition. This facilitates attachment of the needle onto the Luer lock of the needle housing. The modification involves an extension 50 at the first end 18 of the inner barrel and the extension has a sawtooth configuration 51 at its extremity. Similarly, the first end 18 of the outer barrel has an inwardly directed sawtooth configuration 52 adapted to engage with the sawtooth configuration 51 of the inner barrel in the initial or packaged condition of the syringe.

An insert 46 (FIG. 11) differs considerably from the insert 11*a* of the earlier embodiment. The insert 46 is essentially a sleeve that fits snugly within the enlarged bore of the outer barrel and is permanently located in position by an annular flange 47 that locks into the groove 45.

The insert or sleeve 46 has four pairs of opposed flexible fingers 48 that are spaced equidistant around the circumference of the insert. Each of the fingers 48 is connected to the main body of the insert by a thin membrane 49 and is inclined inwardly in its normal state. A space exists between the free ends of each pair of opposed fingers 48 and the space is adapted to accommodate the annular protrusion 40 of the inner barrel 44 when the syringe is in the initial position and prior to the injection stroke. It should be noted also that the extension 50 of the inner barrel 44 includes a second annular protrusion 41 having an inclined face 60 (see FIG. 16 for example) for accommodating the end of spring 20 and retaining the spring end in position. The protrusion 41 has an outer diameter greater than the inner diameter of the insert 46 (and greater than the outer diameter of the remainder of the inner barrel) and therefore serves to prevent the inner barrel from being fully withdrawn from the outer barrel after initial assembly of the syringe. The combination of the step 43 and the protrusion 41 serves to replace the fingers 31 of the first embodiment.

The operation of the syringe of this alternative embodiment is the same as that of the first embodiment. Initially the annular protrusion 40 of the inner barrel is secured between each of the four pairs of fingers 48 (see FIG. 12) so that the inner barrel is locked in position relative to the outer barrel with the respective sawtooth configurations engaged. On the first full depression of the plunger (see FIG. 14) an annular ridge or shelf 33 on the plunger 22, engages with the first four of the fingers 48, that is, the finger of each pair nearest the second end 19. Such engagement causes the fingers to move outwardly and release the inner barrel from securement relative to the outer barrel whereby the action of the spring causes the inner barrel to move to the retracted position as pressure on the plunger is released. This operation is the same as the operation of the first embodiment and culminates when the annular protrusion 41 engages the inner end of the insert 46 (see FIG. 16) and the inner fingers 48 of each pair engage the step 43 of the inner barrel 44. The inner barrel is then permanently locked in position relative to the outer barrel.

Figure 13:
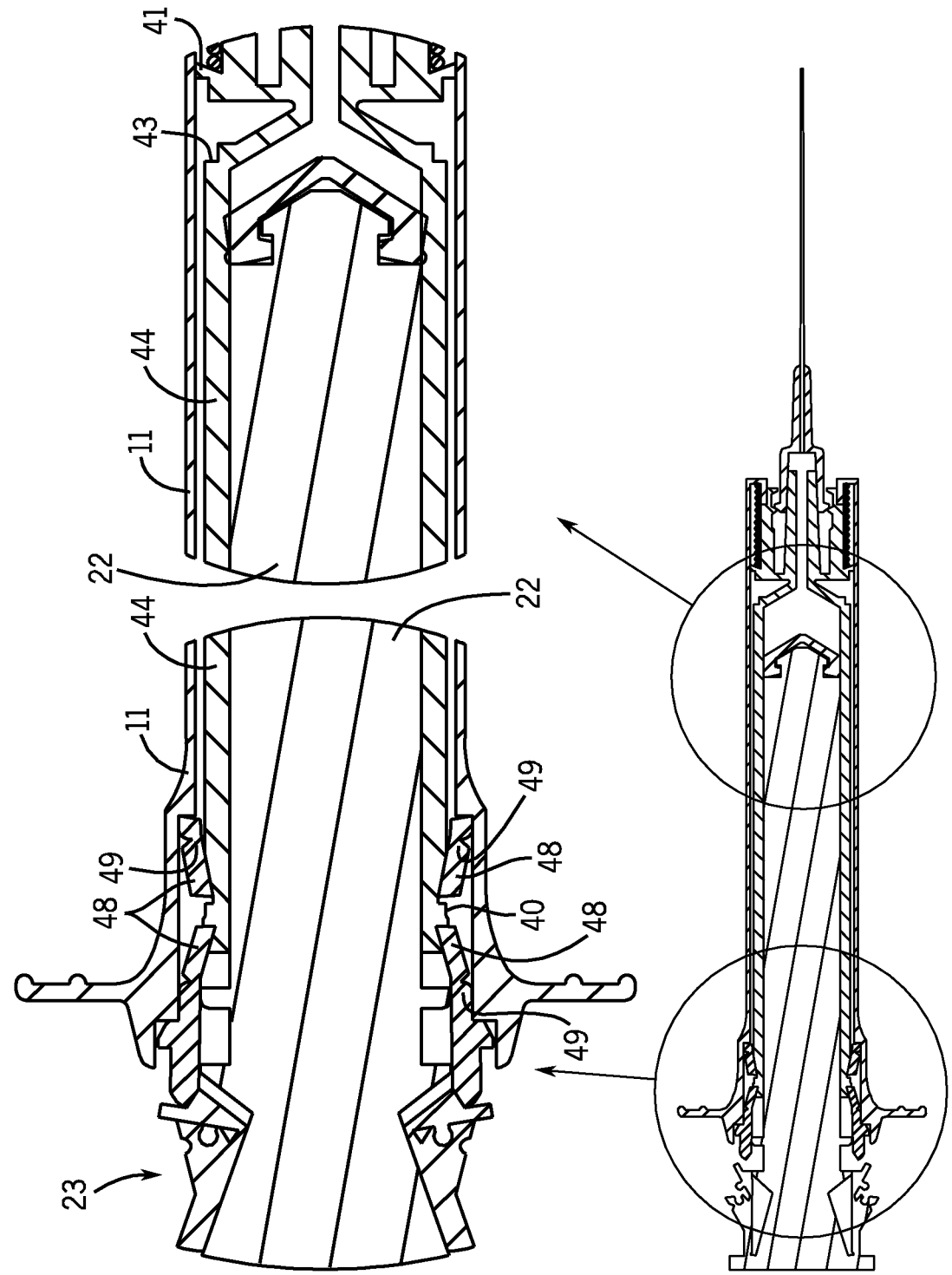
FIG. 13. is a view similar to FIG. 12 showing the alternative embodiment with the parts in position after initial depression of the plunger.
Figure 14:
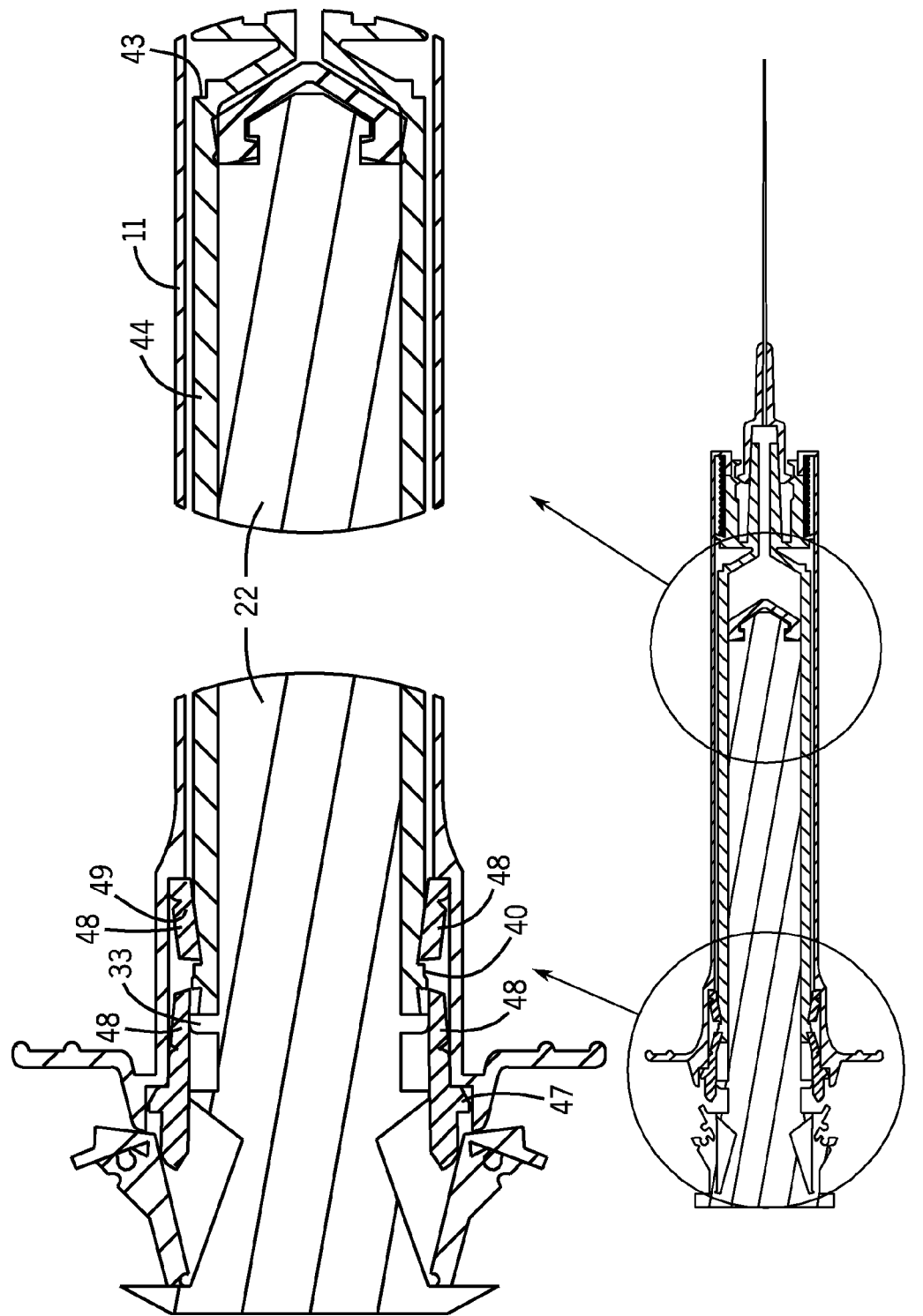
FIG. 14. is a view similar to FIGS. 12 and 13 showing the relative position of the parts after completion of the injection stroke.
Figure 15:
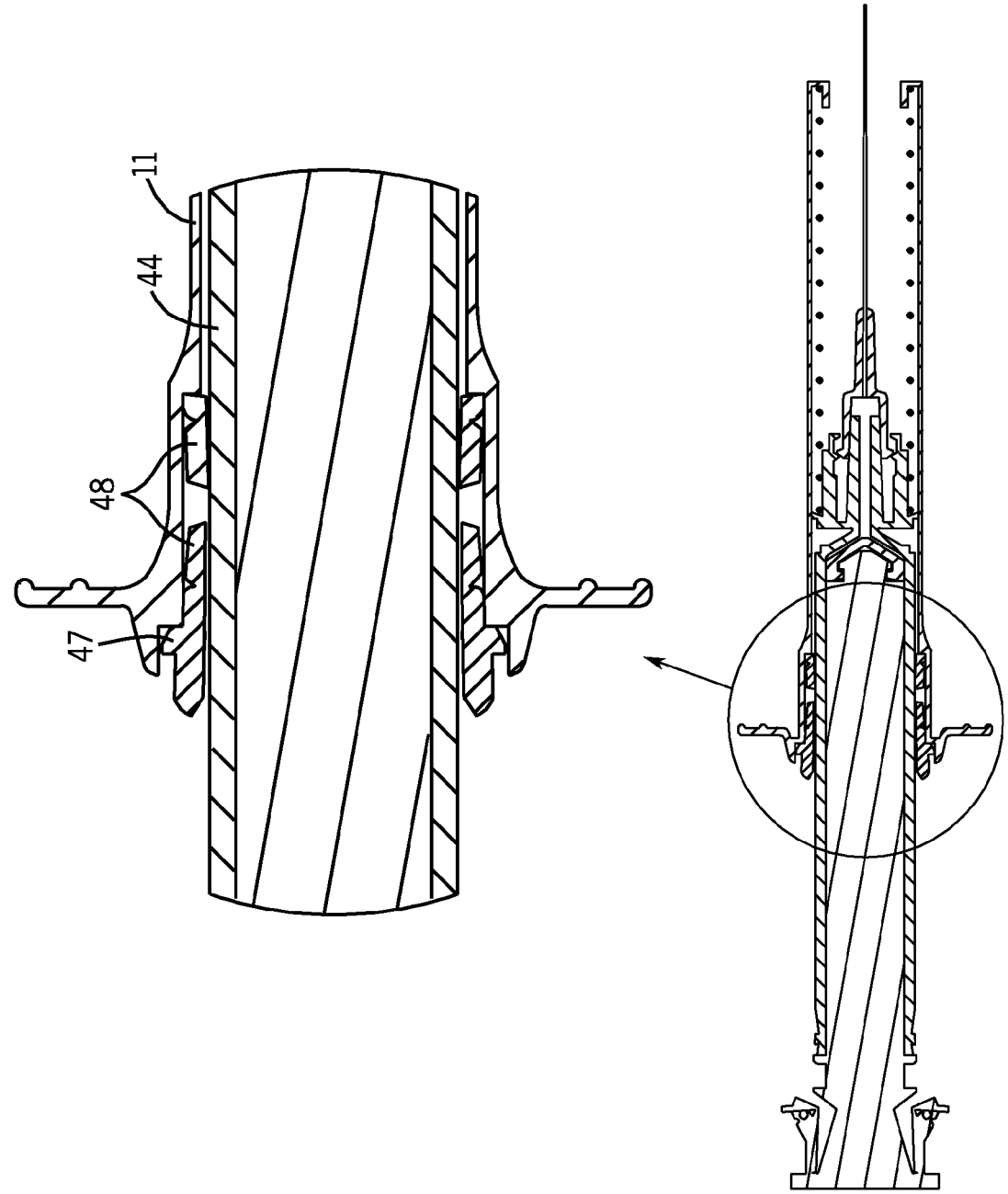
FIG. 15. is a view similar to FIGS. 12-14 showing the relative position of the parts after the injection stroke as the parts move towards the retracted position.
Figure 16:
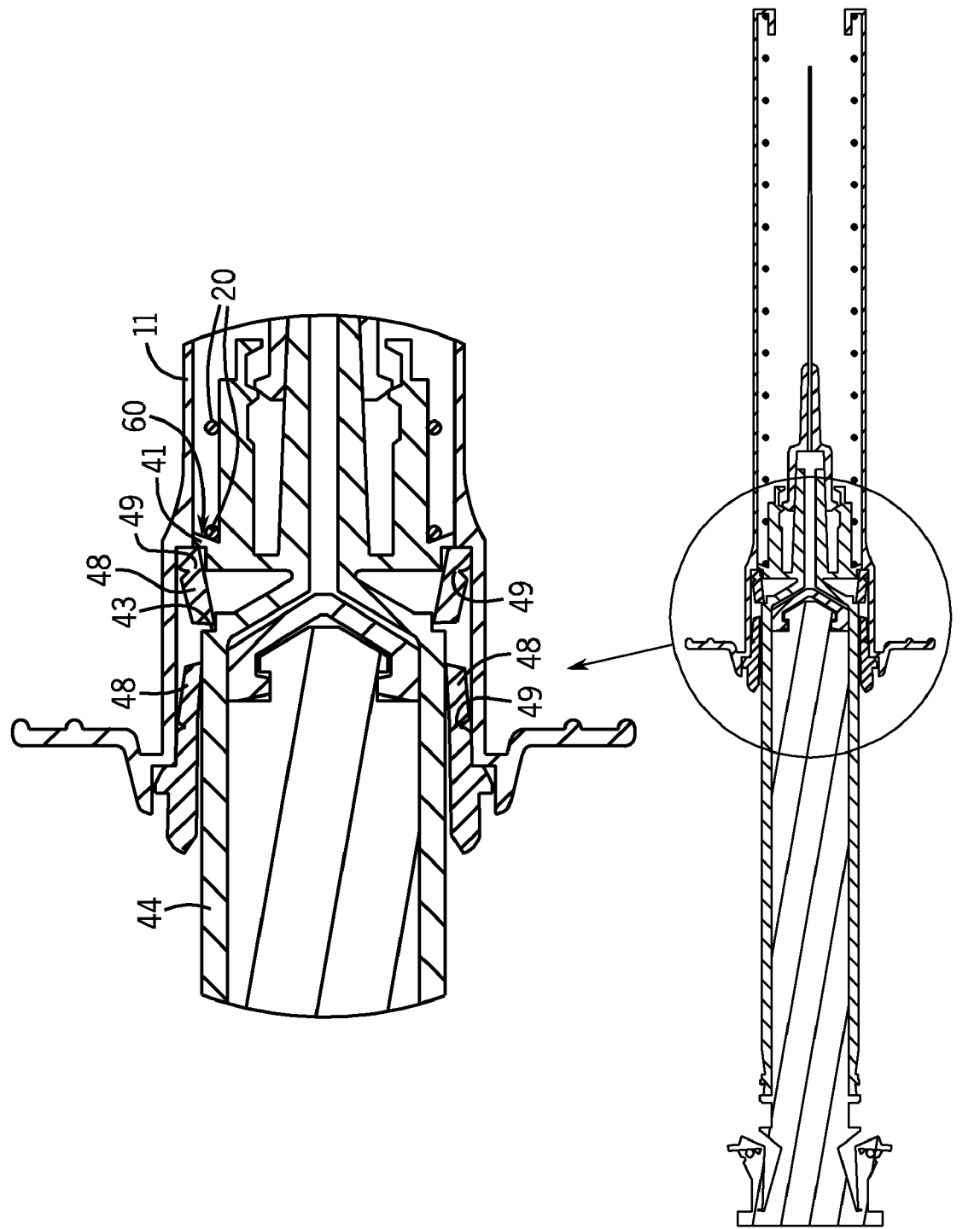
FIG. 16. is a view similar to FIGS. 12-15 showing the relative position of the parts when the syringe is disabled and the needle is fully retracted.

FIG. 13 shows the syringe when the plunger is first depressed from the initial or packaged condition, where the limit catch 23 prevents full depression of the plunger. FIG. 15 shows the condition of the syringe after the injection stroke (full depression of the plunger) and release of pressure on the plunger. The relative position between the inner and outer barrels is shown as the inner barrel moves from the first position to the second or fully retracted position.

Figure 6:
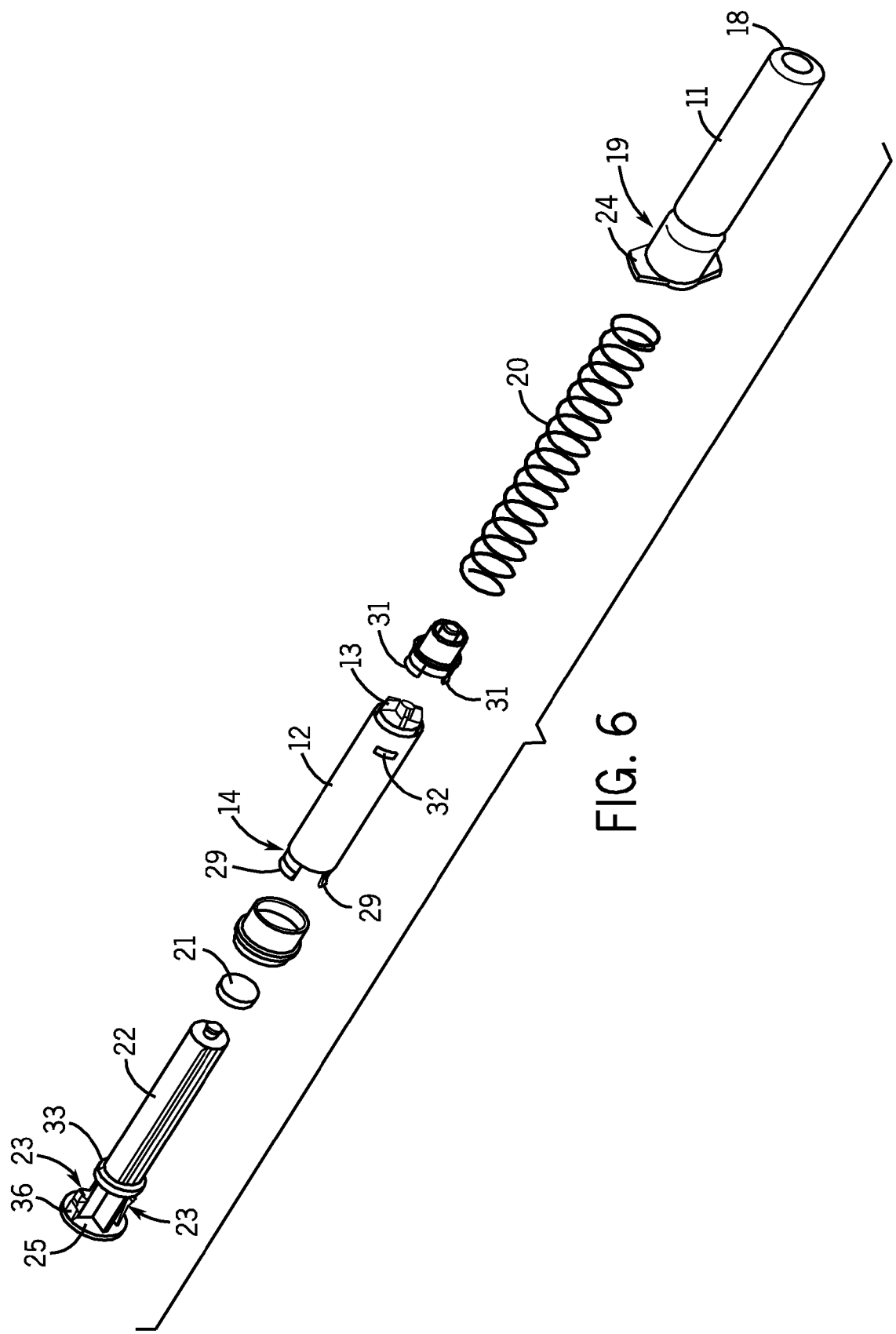
FIG. 6. is a perspective exploded view of the various components of the syringe.
Figure 17:
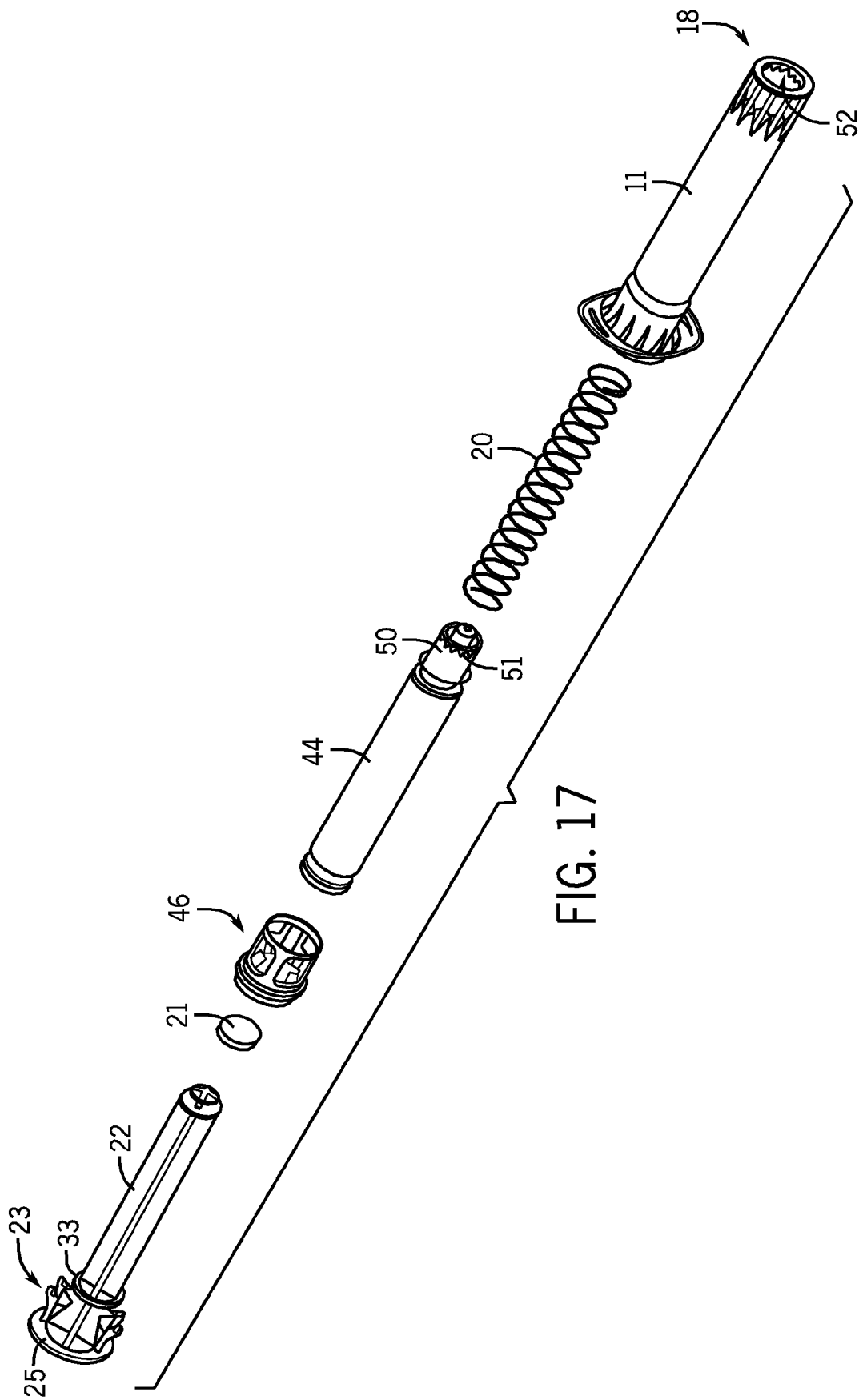
FIG. 17. is a perspective exploded view of the various components of the syringe according to the alternative, more preferred embodiment.

The exploded view of FIG. 17 is similar to FIG. 6 of the first embodiment and like or similar parts have the same reference numeral.

It will be evident to those skilled in the art that the present invention provides a single use retractable syringe that is relatively simple in construction and operation. By having the inner barrel retract to a position where it extends substantially out of the outer barrel, the syringe is able to be made significantly smaller than the syringe described in applicant's earlier International Application referred to hereinabove. In fact, the size of the syringe is solely dependent upon the volume of drug to be injected which governs the size of the inner barrel.

It will be evident also to those skilled in the art that modifications may be readily effected to the above described embodiment without departing from the spirit and scope of the invention described herein.

The claims defining the invention are as follows:

1. A syringe comprising an outer barrel having first and second ends, an inner barrel slidable longitudinally within said outer barrel and adapted to support a needle at one end thereof, which needle projects through an aperture in said first end of said outer barrel and is in fluid communication with a fluid retaining chamber of said inner barrel, a piston within said chamber and actuable to draw fluid into said chamber and expel fluid from said chamber via said needle, a plunger connected to said piston and extending out from the other end of said inner barrel and the second end of said outer barrel, said outer barrel having retaining means on the inner wall surface thereof and said inner barrel having first and second spaced latching means for respectively engaging said retaining means and latching said inner barrel in either of two positions relative to said outer barrel, a first position wherein said needle projects from said outer barrel and is in a useable position, and a second position wherein said needle is fully retracted within said outer barrel, biasing means for biasing said inner barrel towards said second position and said plunger having means thereon to disengage said first latching means from said retaining means when said plunger is fully depressed whereby said inner barrel is able to move to said second position wherein said second latching means engages said retaining means and prevents further relative movement between said inner and outer barrels, and wherein a limit catch is provided on said plunger, said limit catch preventing said plunger from being fully depressed and disengaging said first latching means from said retaining means on initial actuation of said plunger but allowing said plunger to be depressed sufficiently to disengage said first latching means on the next plunger depression;

wherein said inner barrel projects substantially from the second end of said outer barrel when in said second position;

wherein said first latching means comprises an annular protrusion adjacent said other end of said inner barrel, said protrusion being located within a tapered groove in the outer surface of the inner barrel and being adapted for engagement with said retaining means;

wherein said second latching means comprises an annular step at said one end of said inner barrel, in combination with a second annular protrusion spaced a short distance therefrom, said second annular protrusion having an outer diameter greater than the outer diameter of the remainder of the inner barrel;

wherein said retaining means comprises at least one pair of opposed flexible fingers extending in a longitudinal direction of said outer barrel and having a space therebetween for accommodating said annular protrusion, said fingers being inclined inwardly at their adjacent extremities in their normal state, so as to enter said tapered groove and engage said annular protrusion;

wherein said retaining means are provided on an insert which is permanently retained in the second end of said outer barrel and forms part of said outer barrel.

2. A syringe as defined in claim 1, wherein there are four pairs of said opposed flexible fingers spaced equidistant around said insert.

3. A syringe as defined in claim 2, wherein, in said second position of said inner barrel, said annular step is engaged by inwardly directed fingers of each pair to permanently prevent said inner barrel from moving to said first position, and said second annular protrusion engages said insert to prevent said inner barrel from being withdrawn from said outer barrel.

4. A syringe as defined in claim 3, wherein said means on said plunger to disengage said first latching means from said retaining means comprises an annular ridge that engages one of the fingers of each pair and causes the fingers to flex outwardly away from engagement with said annular protrusion at the other end of said inner barrel whereby said inner barrel is able to move from said first to said second position.

5. A syringe comprising an outer barrel having first and second ends, an inner barrel slidable longitudinally within said outer barrel and adapted to support a needle at one end thereof, which needle projects through an aperture in said first end of said outer barrel and is in fluid communication with a fluid retaining chamber of said inner barrel, a piston within said chamber and actuable to draw fluid into said chamber and expel fluid from said chamber via said needle, a plunger connected to said piston and extending out from the other end of said inner barrel and the second end of said outer barrel, said outer barrel having retaining means on the inner wall surface thereof and said inner barrel having first and second spaced latching means for respectively engaging said retaining means and latching said inner barrel in either of two positions relative to said outer barrel, a first position wherein said needle projects from said outer barrel and is in a useable position, and a second position wherein said needle is fully retracted within said outer barrel, biasing means for biasing said inner barrel towards said second position and said plunger having means thereon to disengage said first latching means from said retaining means when said plunger is fully depressed whereby said inner barrel is able to move to said second position wherein said second latching means engages said retaining means and prevents further relative movement between said inner and outer barrels, and wherein a limit catch is provided on said plunger, said limit catch preventing said plunger from being fully depressed and disengaging said first latching means from said retaining means on initial actuation of said plunger but allowing said plunger to be depressed sufficiently to disengage said first latching means on the next plunger depression;

wherein said inner barrel projects substantially from the second end of said outer barrel when in said second position;

wherein said first latching means comprises an annular protrusion adjacent said other end of said inner barrel, said protrusion being located within a tapered groove in the outer surface of the inner barrel and being adapted for engagement with said retaining means;

wherein said second latching means comprises an annular step at said one end of said inner barrel, in combination with a second annular protrusion spaced a short distance therefrom, said second annular protrusion having an outer diameter greater than the outer diameter of the remainder of the inner barrel;

wherein said retaining means comprises at least one pair of opposed flexible fingers extending in a longitudinal direction of said outer barrel and having a space therebetween for accommodating said annular protrusion, said fingers being inclined inwardly at their adjacent extremities in their normal state, so as to enter said tapered groove and engage said annular protrusion;

wherein said retaining means are provided on an insert which is permanently retained in the second end of said outer barrel and forms part of said outer barrel;

wherein there are four pairs of said opposed flexible fingers spaced equidistant around said insert;

wherein, in said second position of said inner barrel, said annular step is engaged by the inwardly directed fingers of each pair to permanently prevent said inner barrel from moving to said first position, and said second annular protrusion engages said insert to prevent said inner barrel from being withdrawn from said outer barrel;

wherein said means on said plunger to disengage said first latching means from said retaining means comprises an annular ridge that engages one of the fingers of each pair and causes the fingers to flex outwardly away from engagement with said annular protrusion at the other end of said inner barrel whereby said inner barrel is able to move from said first to said second position;

wherein a tubular extension is provided on said one end of said inner barrel and said extension has a sawtooth perimeter end at its extremity, said outer barrel having an internally directed sawtooth first said end in opposed relationship to the sawtooth end of said inner barrel, whereby when said inner barrel is in said first position relative to said outer barrel, said respective sawtooth ends are in engagement to prevent relative rotation between said inner and outer barrels.

6. A syringe comprising an outer barrel having first and second ends, an inner barrel slidable longitudinally within said outer barrel and adapted to support a needle at one end thereof, which needle projects through an aperture in said first end of said outer barrel and is in fluid communication with a fluid retaining chamber of said inner barrel, a piston within said chamber and actuable to draw fluid into said chamber and expel fluid from said chamber via said needle, a plunger connected to said piston and extending out from the other end of said inner barrel and the second end of said outer barrel, said outer barrel having retaining means on the inner wall surface thereof and said inner barrel having first and second spaced latching means for respectively engaging said retaining means and latching said inner barrel in either of two positions relative to said outer barrel, a first position wherein said needle projects from said outer barrel and is in a useable position, and a second position wherein said needle is fully retracted within said outer barrel, biasing means for biasing said inner barrel towards said second position and said plunger having means thereon to disengage said first latching means from said retaining means when said plunger is fully depressed whereby said inner barrel is able to move to said second position wherein said second latching means engages said retaining means and prevents further relative movement between said inner and outer barrels, and wherein a limit catch is provided on said plunger, said limit catch preventing said plunger from being fully depressed and disengaging said first latching means from said retaining means on initial actuation of said plunger but allowing said plunger to be depressed sufficiently to disengage said first latching means on the next plunger depression;

wherein said inner barrel projects substantially from the second end of said outer barrel when in said second position;

wherein said first latching means comprises an annular protrusion adjacent said other end of said inner barrel, said protrusion being located within a tapered groove in the outer surface of the inner barrel and being adapted for engagement with said retaining means;

wherein said second latching means comprises an annular step at said one end of said inner barrel, in combination with a second annular protrusion spaced a short distance therefrom, said second annular protrusion having an outer diameter greater than the outer diameter of the remainder of the inner barrel;

wherein said retaining means comprises at least one pair of opposed flexible fingers extending in a longitudinal direction of said outer barrel and having a space therebetween for accommodating said annular protrusion, said fingers being inclined inwardly at their adjacent extremities in their normal state, so as to enter said tapered groove and engage said annular protrusion;

wherein said retaining means are provided on an insert which is permanently retained in the second end of said outer barrel and forms part of said outer barrel;

wherein there are four pairs of said opposed flexible fingers spaced equidistant around said insert;

wherein, in said second position of said inner barrel, said annular step is engaged by the inwardly directed fingers of each pair to permanently prevent said inner barrel from moving to said first position, and said second annular protrusion engages said insert to prevent said inner barrel from being withdrawn from said outer barrel;

wherein said means on said plunger to disengage said first latching means from said retaining means comprises an annular ridge that engages one of the fingers of each pair and causes the fingers to flex outwardly away from engagement with said annular protrusion at the other end of said inner barrel whereby said inner barrel is able to move from said first to said second position;

wherein a tubular extension is provided on said one end of said inner barrel and said extension has a sawtooth perimeter end at its extremity, said outer barrel having an internally directed sawtooth first said end in opposed relationship to the sawtooth end of said inner barrel, whereby when said inner barrel is in said first position relative to said outer barrel, said respective sawtooth ends are in engagement to prevent relative rotation between said inner and outer barrels;

wherein said second annular protrusion is located on said tubular extension and further serves to retain an end of a spring that provides said biasing means.

7. A syringe comprising an outer barrel having first and second ends, an inner barrel slidable longitudinally within said outer barrel and adapted to support a needle at one end thereof, which needle projects through an aperture in said first end of said outer barrel and is in fluid communication with a fluid retaining chamber of said inner barrel, a piston within said chamber and actuable to draw fluid into said chamber and expel fluid from said chamber via said needle, a plunger connected to said piston and extending out from the other end of said inner barrel and the second end of said outer barrel, said outer barrel having retaining means on the inner wall surface thereof and said inner barrel having first and second spaced latching means for respectively engaging said retaining means and latching said inner barrel in either of two positions relative to said outer barrel, a first position wherein said needle projects from said outer barrel and is in a useable position, and a second position wherein said needle is fully retracted within said outer barrel, biasing means for biasing said inner barrel towards said second position and said plunger having means thereon to disengage said first latching means from said retaining means when said plunger is fully depressed whereby said inner barrel is able to move to said second position wherein said second latching means engages said retaining means and prevents further relative movement between said inner and outer barrels, and wherein a limit catch is provided on said plunger, said limit catch preventing said plunger from being fully depressed and disengaging said first latching means from said retaining means on initial actuation of said plunger but allowing said plunger to be depressed sufficiently to disengage said first latching means on the next plunger depression;

wherein said inner barrel projects substantially from the second end of said outer barrel when in said second position;

wherein said inner barrel has stop means on the outer surface thereof, which stop means engage said retaining means when said inner barrel is in said second position to prevent withdrawal of said inner barrel from said outer barrel.

8. A syringe as defined in claim 7, wherein said retaining means comprises an annular groove on the inside of said outer barrel.

9. A syringe as defined in claim 8, wherein said first latching means comprises a first series of flexible fingers arranged on said other end of the inner barrel to engage said annular groove thereby preventing said inner barrel from moving in a direction towards said second position.

10. A syringe as defined in claim 9, wherein said means for contacting said first latching means comprises an annular ridge on said plunger that engages said fingers to cam said fingers inwardly and out of said annular groove on full depression of said plunger, thereby causing said biasing means to move said inner barrel to said second position.

11. A syringe as defined in claim 10, wherein said second latching means comprises a second series of flexible fingers arranged on said one end of said inner barrel.

12. A syringe as defined in claim 11, wherein said stop means comprises abutments on the outer surface of said inner barrel, said abutments engaging said annular groove to prevent removal of said inner barrel from said outer barrel.

13. A syringe as defined in claim 12, wherein said needle is connected to said inner barrel by a Luer connection.

14. A syringe as defined in claim 13, wherein a further annular groove is provided on the inside of said outer barrel adjacent said first end to accommodate said second series of flexible fingers when said inner barrel is in said first position thereby accommodating said fingers in a non-flexed condition.

\* \* \* \* \*

UNITED STATES PATENT AND TRADEMARK OFFICE
CERTIFICATE OF CORRECTION

PATENT NO. : 7,850,647 B2  
APPLICATION NO. : 10/592713  
DATED : December 14, 2010  
INVENTOR(S) : Bruce Wallace Ingram et al.

Page 1 of 1

It is certified that error appears in the above-identified patent and that said Letters Patent is hereby corrected as shown below:

Title Page

Please add:

--(30) Foreign Application Priority Data

Mar. 16, 2004 (AU) .......................... 2004901391--

Signed and Sealed this
Fifth Day of April, 2011

David J. Kappos
*Director of the United States Patent and Trademark Office*